US012285152B2

(12) United States Patent
Nishide et al.

(10) Patent No.: US 12,285,152 B2
(45) Date of Patent: Apr. 29, 2025

(54) PROGRAM, INFORMATION PROCESSING METHOD, AND ENDOSCOPE SYSTEM

(71) Applicant: HOYA CORPORATION, Tokyo (JP)

(72) Inventors: Akihiko Nishide, Tokyo (JP); Junko Sugai, Kanagawa (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 18/278,040

(22) PCT Filed: Apr. 26, 2022

(86) PCT No.: PCT/JP2022/018818
§ 371 (c)(1),
(2) Date: Aug. 21, 2023

(87) PCT Pub. No.: WO2022/270149
PCT Pub. Date: Dec. 29, 2022

(65) Prior Publication Data
US 2024/0122443 A1   Apr. 18, 2024

(30) Foreign Application Priority Data

Jun. 24, 2021 (JP) ................................ 2021-104980

(51) Int. Cl.
 *A61B 1/00* (2006.01)
 *A61B 1/012* (2006.01)
 *A61B 1/045* (2006.01)

(52) U.S. Cl.
 CPC .. *A61B 1/000095* (2022.02); *A61B 1/000094* (2022.02); *A61B 1/000096* (2022.02);
(Continued)

(58) Field of Classification Search
 CPC ........ A61B 1/000095; A61B 1/000094; A61B 1/000096; A61B 1/00057; A61B 1/0125; A61B 1/045
 See application file for complete search history.

(56) References Cited

U.S. PATENT DOCUMENTS 4,951,134 A    8/1990  Nakashima et al.
5,864,361 A    1/1999  Sekiya et al.
(Continued)

FOREIGN PATENT DOCUMENTS

JP    S60-144092 A    7/1985
JP    S61-90636 A     5/1986
(Continued)

OTHER PUBLICATIONS

Extended European Search Report issued in EPO Patent Application No. 22828068.1, dated Oct. 9, 2024.
(Continued)

*Primary Examiner* — Girumsew Wendmagegn
(74) *Attorney, Agent, or Firm* — GREENBLUM & BERNSTEIN, P.L.C.

(57) ABSTRACT

A program causes a computer communicatively connected to an endoscope apparatus provided with a master endoscope and a slave endoscope to execute processing, including acquiring a master endoscope image of a subject from the master endoscope, acquiring a slave endoscope image of the subject from the slave endoscope, and correcting a color tone of at least either one endoscope image of the master endoscope image and the slave endoscope image so as to reduce a difference in color tone between the master endoscope image and the slave endoscope image that have been acquired.

9 Claims, 12 Drawing Sheets

(52) U.S. Cl.
CPC ........ *A61B 1/00057* (2013.01); *A61B 1/0125* (2013.01); *A61B 1/045* (2013.01)

(56) References Cited

U.S. PATENT DOCUMENTS

2012/0224026 A1    9/2012    Bayer et al.
2021/0235053 A1*  7/2021    Hedges .................... A61B 1/05

FOREIGN PATENT DOCUMENTS

| JP | S61-234834 A | 10/1986 |
| JP | H04-297222 A | 10/1992 |
| JP | H04-354929 A | 12/1992 |

OTHER PUBLICATIONS

International Search Report issued in WIPO Patent Application No. PCT/JP2022/018818, dated Jul. 19, 2022, along with an English translation thereof.

\* cited by examiner

PROGRAM, INFORMATION PROCESSING METHOD, AND ENDOSCOPE SYSTEM

TECHNICAL FIELD

The present technology relates to a program, an information processing method, and an endoscope system.

The present application claims priority based on Japanese Patent Application No. 2021-104980 filed on Jun. 24, 2021, the entire contents of which are incorporated herein by reference.

BACKGROUND ART

An endoscope is a medical instrument to be inserted into a body cavity of a subject to observe and treat a desired site that includes an imaging unit provided at a distal tip portion of an insertion tube to be inserted into the body cavity, and an illumination device illuminating an imaging field of view of the imaging unit. Patent Literature 1 discloses, as an endoscope apparatus that observes the inside of a bile duct, a pancreatic duct, or the like, a master scope having an insertion portion that is insertable up to the duodenum and a master-slave scope type endoscope apparatus capable of observing and treating up to a bile duct or a pancreatic duct by inserting a slave scope into a forceps channel of the master scope.

CITATION LIST

Patent Literature

Patent Literature 1: JP 4-354929 A

SUMMARY OF INVENTION

Technical Problem

However, in the endoscope apparatus described in Literature 1, there is a problem in that matters related to color tone correction in an endoscope image imaged by the master scope (master endoscope image) and an endoscope image imaged by the slave scope (slave endoscope image) have not been considered.

In one aspect, an object is to provide a program or the like capable of performing color tone correction on a master endoscope image imaged by the master endoscope and a slave endoscope image imaged by the slave endoscope in an endoscope apparatus provided with the master endoscope and the slave endoscope.

Solution to Problem

A program according to one aspect of the present disclosure causes a computer communicatively connected to an endoscope apparatus provided with a master endoscope and a slave endoscope to execute processing that includes acquiring a master endoscope image of a subject from the master endoscope, acquiring a slave endoscope image of the subject from the slave endoscope, and correcting a color tone of at least either one endoscope image of the master endoscope image and the slave endoscope image so as to reduce a difference in color tone between the master endoscope image and the slave endoscope that have been acquired.

An information processing method according to one aspect of the present disclosure causes a computer communicatively connected to an endoscope apparatus provided with a master endoscope and a slave endoscope to execute processing that includes acquiring a master endoscope image of a subject from the master endoscope, acquiring a slave endoscope image of the subject from the slave endoscope, and correcting a color tone of at least either one endoscope image of the master endoscope image and the slave endoscope image so as to reduce a difference in color tone between the master endoscope image and the slave endoscope that have been acquired.

An endoscope system according to one aspect of the present disclosure is an endoscope system including an endoscope apparatus and control units that process endoscope images of a subject that is imaged, wherein the endoscope apparatus is provided with a master endoscope, a slave endoscope that protrudes from a distal tip portion of the master endoscope, and a detection unit provided on a distal tip side of the master endoscope and which detects the slave endoscope, and when the detection unit detects the slave endoscope, the control unit acquires a master endoscope image of the subject from the master endoscope, acquires a slave endoscope image of the subject from the slave endoscope, and corrects a color tone of at least either one endoscope image of the master endoscope image and the slave endoscope image so as to reduce a difference in color tone between the master endoscope image and the slave endoscope image that have been acquired.

Advantageous Effects of Invention

According to the present disclosure, it is possible to provide a program or the like that performs color tone correction on a master endoscope image imaged by a master endoscope and a slave endoscope image imaged by a slave endoscope in an endoscope apparatus provided with the master endoscope and the slave endoscope.

BRIEF DESCRIPTION OF DRAWINGS

FIG. 4 is a side cross-sectional view that schematically illustrates a slave endoscope or the like.

DESCRIPTION OF EMBODIMENTS

First Embodiment

Figure 1:
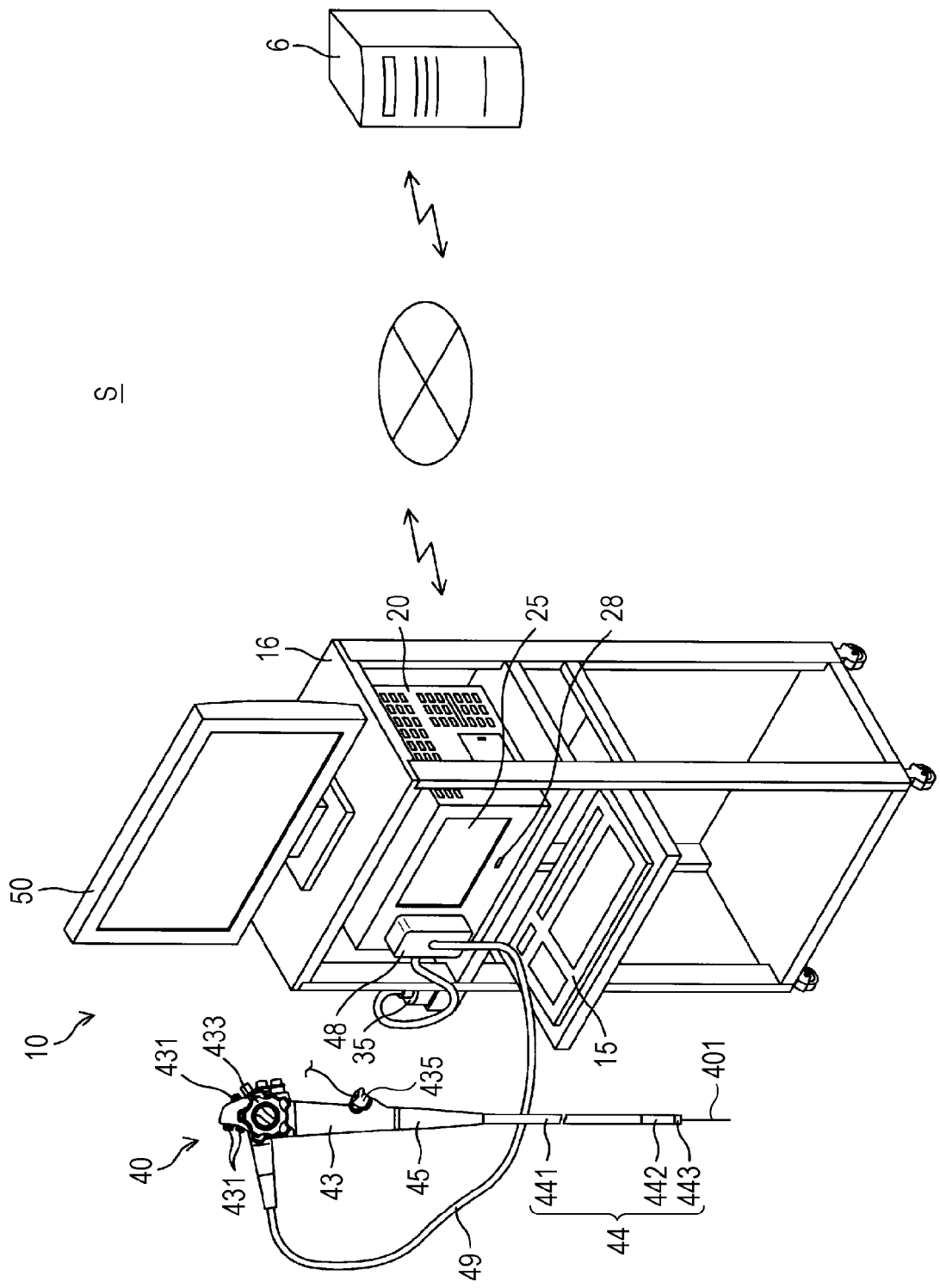
FIG. 1 is a schematic diagram that illustrates an outline of an endoscope system according to a first embodiment.

Hereinafter, the present invention will be described in detail with reference to the drawings illustrating embodiments of the present invention. FIG. 1 is a schematic diagram that illustrates an outline of an endoscope system S according to a first embodiment. The endoscope system S may include an endoscope apparatus 10, and further, may include an information processing apparatus 6 communicatively connected to the endoscope apparatus 10.

The endoscope apparatus 10 transmits images (captured images) captured by image sensors 445 of endoscopes (master endoscope 40 and slave endoscope 401) to a processor 20 for an endoscope, and the processor 20 for an endoscope performs each type of image processing such as gamma correction, white balance correction, and shading correction to generate endoscope images (master endoscope image and slave endoscope image) in a state that is easy to view by an operator. The endoscope apparatus 10 may output (transmit) the endoscope images that are generated to the information processing apparatus 6. For example, the information processing apparatus 6 that has acquired the endoscope images transmitted from the endoscope apparatus 10 performs, for example, various types of information processing and outputs information related to diagnosis assistance based on these endoscope images.

The endoscope apparatus 10 is a master-slave type endoscope apparatus 10 that includes the processor 20 for an endoscope, the master endoscope 40, the slave endoscope 401, and a display device 50. The display device 50 is, for example, a liquid crystal display device or an organic electro luminescence (EL) display device. The master endoscope image is imaged by the master endoscope 40 and the slave endoscope image is imaged by the slave endoscope 401.

The display device 50 is provided on an upper shelf of a storage shelf 16 with casters. The processor 20 for an endoscope is housed on a middle shelf of the storage shelf 16. The storage shelf 16 is disposed in the vicinity of a bed for endoscopic examination (not illustrated). The storage shelf 16 has a pull-out shelf on which a keyboard 15 connected to the processor 20 for an endoscope is provided.

The processor 20 for an endoscope has a substantially rectangular parallelepiped shape and is provided with a touch panel 25 on one surface. A reading unit 28 is disposed at a lower portion of the touch panel 25. The reading unit 28 is, for example, a connection interface for performing reading and writing to a portable recording medium such as a USB connector, a secure digital (SD) card slot, or a compact disc read only memory (CD-ROM) drive.

The master endoscope 40 has an insertion portion 44, an operation unit 43, a master endoscope universal cord 49, and a scope connector 48. The operation unit 43 is provided with a control button 431. The insertion portion 44 is long and one end is connected to the operation unit 43 via a bend preventing portion 45. The insertion portion 44 has, in order from the operation unit 43 side, a soft portion 441, a bending section 442, and a distal tip portion 443. The bending section 442 bends in accordance with the operation of a bending knob 433. Physical detection devices such as a three-axis acceleration sensor, a gyro sensor, a geomagnetic sensor, a magnetic coil sensor, an endoscope-insertion-shaped observation device (colonoscope navigation), or the like may be attached to the insertion portion 44, and detection results from these physical detection devices may be acquired when the master endoscope 40 is inserted into a body of a subject.

The operation unit 43 of the master endoscope 40 is provided with a forceps port 435, and the slave endoscope 401 is inserted inside the master endoscope 40 from the forceps port 435. In other words, the slave endoscope 401 is inserted through a forceps port channel (working channel) provided inside the master endoscope 40 and protrudes from the distal tip portion 443 of the master endoscope 40.

The master endoscope universal cord 49 is long, and a first end is connected to the operation unit 43, while a second end is connected to the scope connector 48. The master endoscope universal cord 49 is soft. The scope connector 48 has a substantially rectangular parallelepiped shape. The scope connector 48 is provided with an air/water supply port 36 (see FIG. 2) to be connected to an air/water supply tube. A slave endoscope universal cord 491 is connected to the scope connector 48 in the same way as the master endoscope universal cord 49. The master endoscope universal cord 49 and the slave endoscope universal cord 491 may be integrated and shared by the master endoscope 40 and the slave endoscope 401.

Figure 2:
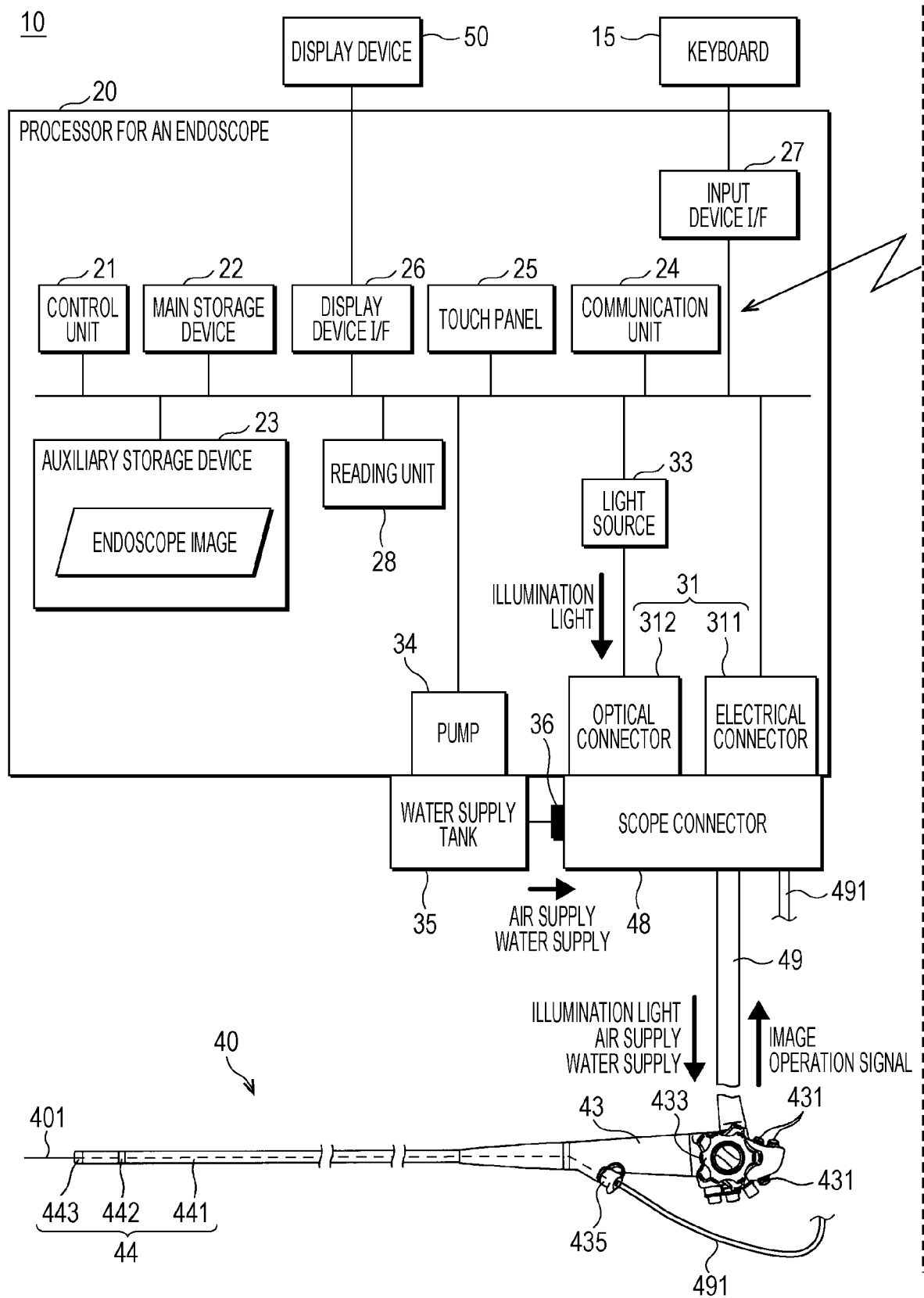
FIG. 2 is a block diagram that illustrates a configuration example of an endoscope apparatus included in the endoscope system.

FIG. 2 is a block diagram that illustrates a configuration example of an endoscope apparatus included in the endoscope system. A control unit 21 is an arithmetic control device that executes a program according to the present embodiment. One or a plurality of central processing units (CPUs), graphics processing units (CPUs), multi-core CPUs, and the like is used for the control unit 21. The control unit 21 is connected to each hardware unit constituting the processor 20 for an endoscope via a bus.

A main storage device 22 is, for example, a storage device such as a static random-access memory (SRAM), a dynamic random-access memory (DRAM), or a flash memory. The main storage device 22 temporarily stores information necessary during the processing performed by the control unit 21 and a program being executed by the control unit 21. An auxiliary storage device 23 is, for example, a storage device such as a SRAM, a flash memory, or a hard disk, and is a storage device with a larger capacity than the main storage device 22. The auxiliary storage device 23 may store, for example, the captured images that are acquired from the master endoscope image and the slave endoscope image (master captured image and slave captured image) and the endoscope images that are generated (master endoscope image, slave endoscope image) as intermediate data.

A communication unit 24 is a communication module or a communication interface for wired or wirelessly communicating with the information processing apparatus 6 via a network and is, for example, a narrow-area wireless communication module such as Wi-Fi (registered trademark) or Bluetooth (registered trademark), or a wide-area wireless communication module such as 4G or 5G. The touch panel 25 includes a display unit such as a liquid crystal display panel and an input unit layered on the display unit. The communication unit 24 may communicate with a CT apparatus, an MRI apparatus (see FIG. 8), an ultrasonic diagnosis apparatus, or a storage device (not illustrated) that stores data output from these apparatuses.

A display device I/F 26 is an interface to be connected to the processor 20 for an endoscope and the display device 50. An input device I/F 27 is an interface to be connected to the processor 20 for an endoscope and an input device such as the keyboard 15.

A light source 33 is, for example, a high-luminance white light source such as a white LED or a xenon lamp. The light source 33 is connected to the bus via a driver (not illustrated). The control unit 21 controls switching the light source 33 on and off and changing luminance. Illumination light emitted from the light source 33 is incident on an optical connector 312. The optical connector 312 engages with the scope connector 48 to supply illumination light to the master endoscope 40 and the slave endoscope 401. The light source 33 may be shared by the master endoscope 40 and the slave endoscope 401, or the light source 33 may be provided as individual light sources 33 for the master endoscope 40 and the slave endoscope 401. Alternatively, the light source 33 (light source for an endoscope) may be a master endoscope 40 or a slave endoscope 401 having a structure in which an LED for a light source is attached at the distal tip portion.

A pump 34 generates pressure for an air/water supply function of the master endoscope 40. The pump 34 is connected to the bus via a driver (not illustrated). The control unit 21 controls switching the pump 34 on and off and changing pressure. The pump 34 is connected to the air/water supply port 36 provided on the scope connector 48 via a water supply tank 35.

An outline of functions of the endoscopes (master endoscope 40 and slave endoscope 401) connected to the processor 20 for an endoscope will be described. A fiber bundle, a cable bundle, an air supply tube, a water supply tube, and the like are inserted inside the scope connector 48, the master endoscope universal cord 49, the slave endoscope universal cord 491, the operation unit 43, and the insertion portion 44. Illumination light emitted from the light source 33 is radiated from illumination windows provided at the distal tips of the master endoscope 40 and the slave endoscope 401 via the optical connector 312 and the fiber bundle. A range illuminated by the illumination light is captured by each of the image sensors provided at the respective distal tips of the master endoscope 40 and the slave endoscope 401. The image sensors of the master endoscope 40 and the slave endoscope 401 each transmit captured images (master captured image and slave captured image) to the processor 20 for an endoscope via the cable bundle and an electrical connector 311.

The control unit 21 of the processor 20 for an endoscope functions as an image processing unit 211 by executing a program stored in the main storage device 22. The image processing unit 211 performs each type of image processing such as gamma correction, white balance correction, and shading correction on the captured images (master captured image and slave captured image) output from the endoscopes (master endoscope 40 and slave endoscope 401), and outputs the result as endoscope images (master endoscope image, slave endoscope image).

Figure 3:
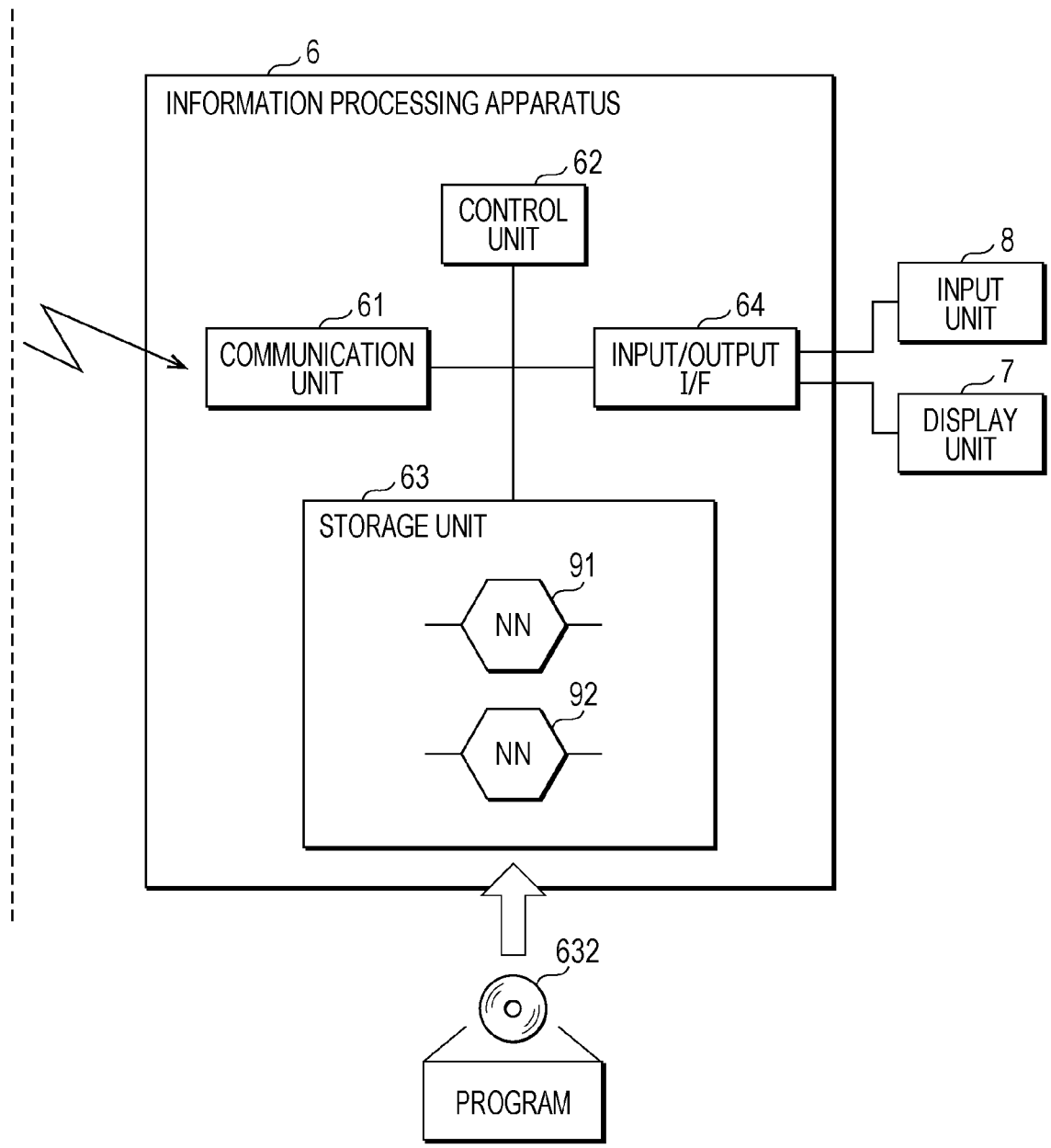
FIG. 3 is a block diagram that illustrates a configuration example of an information processing apparatus included in the endoscope system.

FIG. 3 is a block diagram that illustrates a configuration example of the information processing apparatus included in the endoscope system. The information processing apparatus 6 includes a control unit 62, a communication unit 61, a storage unit 63, and an input/output I/F 64. The information processing apparatus 6 is, for example, a server device or a personal computer. The server device not only includes a single server device, but also a cloud server device configured by a plurality of computers, or a virtual server device. The information processing apparatus 6 may be provided as a cloud server located on an external network accessible from the processor 20 for an endoscope.

The control unit 62 includes one or a plurality of arithmetic processing devices provided with a time counting function, such as a central processing unit (CPU), a microprocessing unit (MPU), and a graphics processing unit (GPU), and performs various types of information processing, control processing, and the like related to the information processing apparatus 6 by reading and executing a program P stored in the storage unit 63.

The storage unit 63 includes a volatile storage area such as a static random-access memory (SRAM), a dynamic random-access memory (DRAM), or a flash memory, and a nonvolatile storage area such as an EEPROM or a hard disk. The storage unit 63 stores the program P (program product) and data to be referred to at the time of processing in advance. The program P (program product) stored in the storage unit 63 may be stored as a program P (program product) that is read from a recording medium 632 readable by the information processing apparatus 6. In addition, the program P (program product) may be downloaded from an external computer (not illustrated) connected to a communication network (not illustrated) and stored in the storage unit 63. The storage unit 63 stores entity files (instance files of a neural network (NN)) constituting a plurality of learning models (91, 92) according to a second embodiment, etc. to be described later. These entity files may be configured as one part of the program P (program product).

The communication unit 61 is a communication module or a communication interface for wired or wirelessly communicating with the endoscope apparatus 10, and is, for example, a narrow-area wireless communication module such as Wi-Fi (registered trademark) or (registered trademark), or a wide-area wireless communication module such as 4G or LTE. The communication unit 61 may communicate with a CT apparatus, an MRI apparatus (see FIG. 8), an ultrasonic diagnosis apparatus, or a storage device (not illustrated) that stores data output from these apparatuses.

The input/output I/F 64 is a communication interface that conforms, for example, to a communication standard such as USB or DSUB, and is for serially communicating with an external apparatus connected to the input/output I/F 64. For example, a display unit 7 such as a display, and an input unit 8 such as a keyboard are connected to the input/output I/F 64, and the control unit 62 outputs, to the display unit 7, a result of information processing performed based on an execution command or an event input from the input unit 8.

Figure 4:
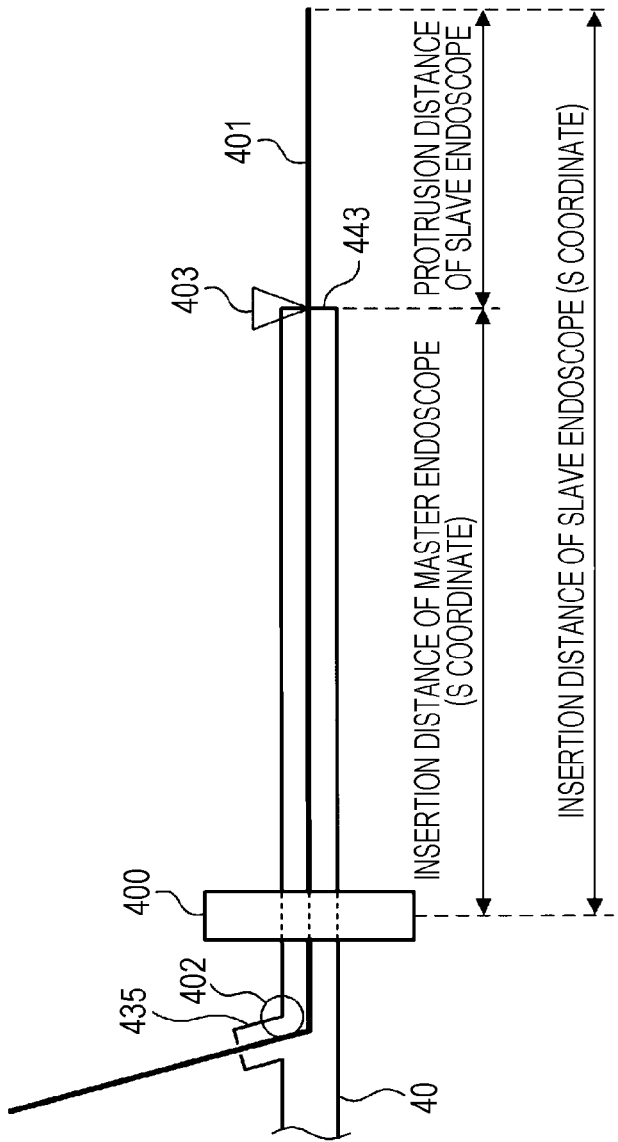

FIG. 4 is a side cross-sectional view that schematically illustrates the slave endoscope 401 or the like. As described above, the slave endoscope 401 is inserted from the forceps port 435 provided in the master endoscope 40, is inserted through (passes through) the forceps port channel (working channel), and protrudes from the distal tip portion 443 of the master endoscope 40. The master endoscope 40 is, for example, a duodenoscope, and corresponds to a master scope, while the slave endoscope 401 is, for example, a biliary tract endoscope, and corresponds to a slave scope. The insertion portion 44 (flexible tube) of the master endoscope 40 is provided with, for example, a master endoscope measurement unit 400 configured by a roller encoder or the like, and measures an S coordinate, which is a distance at which the master endoscope 40 is inserted into the body.

The master endoscope measurement unit 400 includes, for example, a temperature sensor, an optical sensor, a pressure sensor, a wetness sensor (electrode), and a humidity sensor. When the sensor is, for example, an optical sensor, the optical sensor is disposed inside the insertion portion 44 (flexible tube), however the optical sensor can also receive light even when the insertion portion 44 (flexible tube) is inserted into the body. Therefore, it is possible to determine that a section at which the optical sensor receives more light is outside the body, while a section at which the optical sensor receives less light is inside the body. Also, the control unit 21 of the processor 20 for an endoscope can derive the S coordinate (S coordinate of the master endoscope 40), which is the distance (length) at which the insertion portion 44 (flexible tube) is inserted into the body, by specifying the optical sensor located at a boundary position, which is a body cavity insertion site, based on a signal obtained by the optical sensor.

When the master endoscope 40 is an upper endoscope, the master endoscope measurement unit 400 is attached connected to the insertion portion 44 (flexible tube), and the S coordinate, which is the distance at which the master endoscope 40 is inserted into the body, can be acquired using the roller encoder of the master endoscope measurement unit 400, which only rotates along the distance at which the insertion portion 44 (flexible tube) is inserted into the body. A mouthpiece or the like (roller encoder) constituting master endoscope measurement unit 400 rotates with the forward and backward movement of the insertion portion 44 (flexible tube), and can measure a length between the distal tip portion 443 of the master endoscope 40 inserted into the body and, for example, an opening portion joining with a cavity, such as a mouth or a nose, that is, the insertion distance of the insertion portion 44 (flexible tube). The roller encoder is electrically connected to the processor 20 for an endoscope, and transmits the measured distance to the processor 20 for an endoscope. In addition, an optical encoder or a magnetic encoder may be used instead of the roller encoder.

When the master endoscope 40 is a lower endoscope, an insertion distance of the endoscope can be measured by attaching the master endoscope measurement unit 400 corresponding to the mouthpiece to an anal portion. When the master endoscope measurement unit 400 (auxiliary device) that measures the insertion distance of the master endoscope 40 is attached to the body cavity insertion site, which is an entry point of the subject, it is possible to acquire the S coordinate, which is the distance at which the master endoscope 40 is inserted into the body, by measuring a passing distance of the master endoscope 40. The auxiliary device may, for example, measure a distance by a scale of a magnetic field such as a linear scale attached to the insertion portion (flexible tube) 44 and a linear head attached to the mouthpiece, or may be the mouthpiece of the master endoscope 40 to which a roller is attached. Note that when the master endoscope 40 is inserted into a nose, an anus, or the like, a master endoscope measurement unit 400 (auxiliary device) to which a roller similar to the mouthpiece is attached may be used. A chip in which an insertion distance is recorded at fixed intervals may be incorporated in the insertion portion (flexible tube) 44 of the endoscope 40. The processor 20 for an endoscope can acquire the S coordinate, which is the distance at which the master endoscope 40 is inserted into the body, from S coordinate information recorded in the chip and obtained by the mouthpiece or the like.

A slave endoscope measurement unit 402 configured by, for example, a roller encoder, a magnetic linear encoder, or an optical linear encoder is provided in the vicinity of the forceps port 435 into which the slave endoscope 401 is inserted, in the same way as the master endoscope measurement unit 400. A detection unit 403 (slave endoscope detection unit) that detects the slave endoscope 401 is provided at the distal tip portion 443 of the master endoscope 40, that is, an end portion of the forceps port channel (working channel) through which the slave endoscope 401 is inserted. The detection unit 403 is configured by, for example, a non-contact sensor such as an optical sensor, a contact sensor, or a contact switch, and outputs whether the slave endoscope 401 is present or absent in a sensing range of the optical sensor as a detection result. The detection unit 403 corresponds to an insertion start detection means that detects that insertion of the slave endoscope 401 into the body from the end portion of the forceps port channel (working channel) has started.

When the distal tip of the slave endoscope 401 protrudes from the distal tip portion 443 of the master endoscope 40, the detection unit 403 outputs a detection result indicating that the slave endoscope 401 is present. When the distal tip of the slave endoscope 401 does not protrude from the distal tip portion 443 of the master endoscope 40, the detection unit 403 outputs a detection result indicating that the slave endoscope 401 is absent. When the distal tip of the slave endoscope 401 does not protrude from the distal tip portion 443 of the master endoscope 40, the detection unit 403 may be set to not output any signal or the like.

As described above, an S coordinate (SP), which is the distance at which the master endoscope 40 is inserted into the body, is output as the measurement result by the master endoscope measurement unit 400. When the detection unit 403 outputs the detection result indicating that the slave endoscope 401 is present, the slave endoscope measurement unit 402 outputs the distance at which the slave endoscope 401 is inserted from a point in time when the detection result is output as a protrusion distance (SC). That is, the protrusion distance (SC) indicates a length of the slave endoscope 401 protruding from the distal tip portion 443 of the master endoscope 40.

The S coordinate (S), which is the distance at which the slave endoscope 401 is inserted into the body, is calculated by adding the protrusion distance (SC) at which the slave endoscope 401 is inserted into the body from the point in time when the detection result (the slave endoscope 401 is present) detected by the detection unit 403 is output, to the S coordinate (SP), which is the distance at which the master endoscope 40 is inserted into the body (the S coordinate of the slave endoscope 401=the S coordinate [SP] of the master endoscope 40+the protrusion distance [SC] of the slave endoscope 401). The S coordinate of the slave endoscope 401 is calculated by the control unit 62 of the information processing apparatus 6 or the control unit 21 of the processor 20 for an endoscope based on the S coordinate of the master endoscope 40 and the protrusion distance of the slave endoscope 401.

Figure 5:
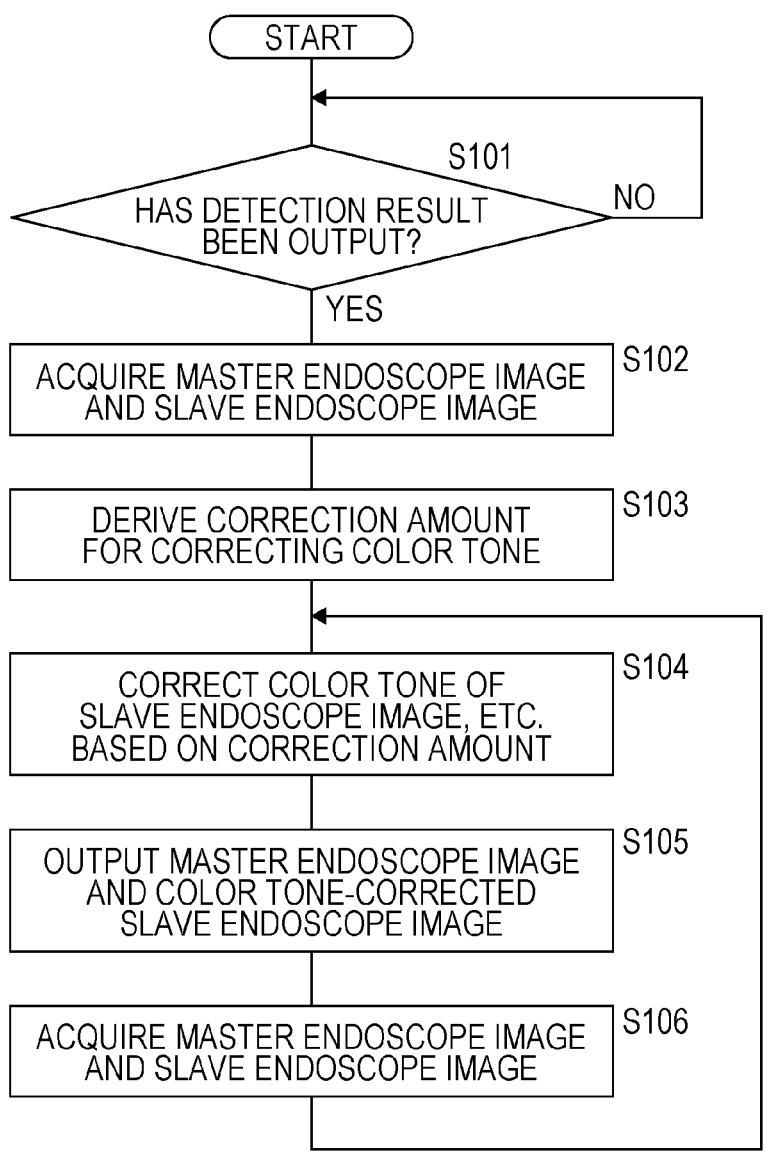
FIG. 5 is a flowchart that illustrates one example of a processing procedure executed by a control unit of a processor for an endoscope.

FIG. 5 is a flowchart that illustrates one example of a processing procedure executed by the control unit 21 of the processor 20 for an endoscope. The control unit 21 of the processor 20 for an endoscope starts processing of the flowchart based on, for example, contents input from the keyboard 15 connected to a local device.

The control unit 21 of the processor 20 for an endoscope determines whether or not a detection result has been output from the detection unit 403 (S101). The control unit 21 of the processor 20 for an endoscope determines from the detection unit 403 whether or not a detection result indicating that the slave endoscope 401 has protruded from the distal tip portion 443 of the master endoscope 40 has been output. That is, when the control unit 21 of the processor 20 for an endoscope acquires a detection result from the detection unit 403, the control unit 21 determines that the slave endoscope 401 has protruded from the distal tip portion 443 of the master endoscope 40, and when the control unit 21 does not acquire a detection result from the detection unit 403, the control unit 21 determines that the slave endoscope 401 has not protruded from the distal tip portion 443 of the master endoscope 40. When a detection result has not been output from the detection unit 403 (S101: NO), the control unit 21 of the processor 20 for an endoscope performs loop processing to execute the process of S101 again.

When a detection result has been output from the detection unit 403 (S101: YES), the control unit 21 of the processor 20 for an endoscope acquires the master endoscope image and the slave endoscope image (S102). When the detection result has been output from the detection unit 403, at the point in time when the detection result is output, the distal tip of the slave endoscope 401 is positioned at the distal tip portion 443 of the master endoscope 40, and a field of view of the master endoscope 40 and a field of view of the slave endoscope 401 coincide with each other. That is, both viewpoint positions of the master endoscope 40 and the slave endoscope 401 are the distal tip portion 443 of the master endoscope 40, and the line-of-sight directions of the master endoscope 40 and the slave endoscope 401 also coincide with each other. From the viewpoint of a viewing angle, that is, an imaging range, the viewing angle of the master endoscope 40 is larger (wider) than the viewing angle of the slave endoscope 401. Consequently, at the point in time when the detection result is output, that is, at the point in time (state) when the distal tip of the slave endoscope 401 is positioned at the distal tip portion 443 of the master endoscope 40, the slave endoscope image of the slave endoscope 401 indicates the same internal body site as a central portion region of the master-slave endoscope image of the master endoscope 40.

The control unit 21 of the processor 20 for an endoscope derives correction amounts for correcting the color tone based on the central portion of the master endoscope image and the slave endoscope image that have been acquired (S103). Since the central portion of the master endoscope image and the slave endoscope image acquired at the point in time when the detection result is output indicate the same internal body site, the central portion of the master endoscope image and the slave endoscope image have essentially the same color tone, that is, the same hue, luminosity, and saturation. However, due to a difference in camera characteristics or AD conversion characteristics between the master endoscope 40 and the slave endoscope 401, a difference in color tone occurs between each of the respective captured endoscope images (master endoscope image, slave endoscope image) despite the endoscope images being the same internal body site (imaged subject).

The control unit 21 of the processor 20 for an endoscope compares, for example, each respective pixel in the central portion region of the master endoscope image with each respective pixel of the slave endoscope image, and derives the difference values of the RGB components (intensity) of each pixel. When only the color tone of the slave endoscope image is corrected with reference to the color tone of the master endoscope image (one-way correction to the master side), the control unit 21 of the processor 20 for an endoscope subtracts the respective RGB values (intensities) of the slave endoscope image corresponding to the pixels from the respective RGB values (intensities) of the pixels in the central portion region of the master endoscope image. The control unit 21 of the processor 20 for an endoscope derives the difference values for the respective RGB values (intensities) of each pixel calculated by subtraction as the correction amounts for color tone correction. The correction amounts may be defined as a data set or a vector consisting of the respective correction values (difference values) for RGB. The respective RGB values (intensities) are, for example, indicated in 256 stages from 0 to 255, and in this case, the correction amounts are, at a maximum, defined in a range of ±255 inclusive.

The control unit 21 of the processor 20 for an endoscope may specify a plurality of pixels in the image coordinate system of the master endoscope image by selecting the plurality of pixels in the image coordinate system of the slave endoscope image and converting the coordinates of the plurality of pixels (the image coordinate system of the slave endoscope image) into the image coordinate system of the master endoscope image when specifying the respective corresponding pixels of the master endoscope image (central portion) and the slave endoscope image. The control unit 21 of the processor 20 for an endoscope may extract a region of the coinciding internal body sites in the central portion of the master endoscope image and the slave endoscope image by, for example, edge detection, and derive a conversion coefficient for the coordinate system conversion based on the coordinate values of the respective image coordinate systems of the master endoscope image and the slave endoscope image specified by a peripheral line around the region. Correction amounts may be derived in units of each pixel in the slave endoscope image, and the derived correction amounts may be respectively applied (added) to individual pixels to correct the color tone of the slave endoscope image. By doing so, the RGB components (intensities) and RGB ratios of the pixels in the slave endoscope image and the master endoscope image can be made equal, and the difference in color tone between the master endoscope image and the slave endoscope image can be reduced to approximate tints.

The control unit 21 of the processor 20 for an endoscope may correct the color tone of the slave endoscope image by deriving the correction amounts based on, for example, average difference values obtained by averaging the respective difference values between a plurality of corresponding pixels in the slave endoscope image and the master endoscope image and uniformly correcting (converting the pixel values of) all the pixels in the slave endoscope image by the correction amounts. Alternatively, in the central portion of the master endoscope image and the slave endoscope image, the component amounts of hue, luminosity, or saturation across the entire image may be calculated, and the correction amounts may be derived based on the difference values of these component amounts.

The control unit 21 of the processor 20 for an endoscope stores the derived correction amounts in the main storage device 22 or the like. After the present processing, the correction amounts stored in the main storage device 22 or the like are used as the correction amounts (correction parameters) of the color tone correction on the slave endoscope image that has been acquired. That is, deriving the correction amounts in the present processing corresponds to calibration for performing the color tone correction on the slave endoscope image. The control unit 21 of the processor 20 for an endoscope may acquire information related to the type, model, or specification of the connected master endoscope 40 and slave endoscope 401, and may, for example, acquire and apply calibration data (correction amounts)

stored in advance in the main storage device 22 based on this information. That is, in the main storage device 22 of the processor 20 for an endoscope, the calibration data (correction amounts) corresponding to each of a plurality of types (models or the like) of the slave endoscope 401 may, for example, be stored (registered) in advance at the time of manufacture, while the control unit 21 of the processor 20 for an endoscope may acquire and apply the corresponding calibration data (correction amounts) in accordance with the connected slave endoscope 401 or in accordance with the combination of the connected slave endoscope 401 and master endoscope 40.

The control unit 21 of the processor 20 for an endoscope corrects the color tone of the slave endoscope image or the like based on the derived correction amounts (S104). For example, the control unit 21 of the processor 20 for an endoscope adds the correction amounts to each pixel of the slave endoscope image to convert the pixel value (RGB intensity) of each pixel, thereby correcting the color tone of the slave endoscope image. When correcting the color tone, the control unit 21 of the processor 20 for an endoscope may change the correction parameters used for various types of image processing such as gamma correction, white balance correction, and shading correction at the time of generating (converting) the endoscope images from the imaged images (raw images) based on the derived correction amounts, and may perform the color tone correction together with processing steps such as the gamma correction.

In the present embodiment, the color tone of the slave endoscope image has been set as being corrected based on the derived correction amounts, however the present invention is not limited hereto. The control unit 21 of the processor 20 for an endoscope may derive correction amounts for correcting the color tone of the master endoscope image, and may correct only the color tone of the master endoscope image with reference to the color tone of the slave endoscope image (one-way correction to the slave side). Alternatively, the control unit 21 of the processor 20 for an endoscope may derive the respective correction amounts for correcting the color tone of the master endoscope image and the slave endoscope image, and correct the color tones of both the master endoscope image and the slave endoscope image (two-way correction).

The control unit 21 of the processor 20 for an endoscope outputs the master endoscope image and the color tone-corrected slave endoscope image (S105). The control unit 21 of the processor 20 for an endoscope outputs the master endoscope image, and the slave endoscope image in which the difference in color tone from the master endoscope image has been reduced by the color tone correction to, for example, the display device 50, or the display unit 7 via the information processing apparatus 6, and displays the master endoscope image and the slave endoscope image subjected to processing related to the color tone correction on the display device 50 or the like. Needless to say, when the color tone of the master endoscope image is corrected as described above, the control unit 21 of the processor 20 for an endoscope outputs the color tone-corrected master endoscope image. It is possible to provide useful medical information to a doctor or the like by outputting the master endoscope image and the slave endoscope image in which the processing related to color tone correction are performed in this way and the difference in color tone is reduced, and displaying on the display unit 7. When displaying the master endoscope image and the slave endoscope image in which the difference in color tone is reduced on the display device 50 or the display unit 7, the control unit 21 of the processor 20 for an endoscope may be caused to display the color tone-corrected slave endoscope image and the slave endoscope image prior to color tone correction in a switchable manner.

The control unit 21 of the processor 20 for an endoscope acquires the master endoscope image and the slave endoscope image (S106). After executing S106, the control unit 21 of the processor 20 for an endoscope performs loop processing to perform the processing from S104 again. By doing so, it is possible to continue the color tone correction using the correction amounts even on a slave endoscope image or the like acquired after the correction amounts have been derived, then reduce the difference in color tone between the master endoscope image and the slave endoscope image and output (display) the master endoscope image and the slave endoscope image.

In the present embodiment, the control unit 21 of the processor 20 for an endoscope has been set to perform a series of processes, however the present invention is not limited hereto. The control unit 21 of the processor 20 for an endoscope may perform, for example, inter-process communication with the control unit 62 of the information processing apparatus 6 to perform a series of processes in cooperation or in a shared manner. Alternatively, the control unit 21 of the processor 20 for an endoscope may generate endoscope images (master endoscope image and slave endoscope image) obtained by only performing various types of image processing such as shading correction on each of the master captured image (raw image) imaged by the master endoscope 40 and the master captured image (raw image) imaged by the master endoscope 40. On doing so, the control unit 62 of the information processing apparatus 6 may perform a series of processes related to the color tone correction on the master endoscope image and the slave endoscope image generated by the control unit 21 of the processor 20 for an endoscope.

According to the present embodiment, etc., it is possible to provide endoscope images (master endoscope image and slave endoscope image) having improved visibility to an operator of an endoscope apparatus such as a doctor or the like by reducing the difference in color tone between the master endoscope image and the slave endoscope image and bringing the tints of both images close to each other. By providing the doctor or the like with the master endoscope image and the slave endoscope image that have been corrected so that the difference in color tone is reduced in this way, it is expected that discomfort or difficulty in diagnosis by the doctor or the like is alleviated.

According to the present embodiment, etc., at the point in time when the slave endoscope 401 protrudes from the distal tip portion 443 of the master endoscope 40, that is, at the point in time when the distal tip of the slave endoscope 401 is positioned at the distal tip portion 443 of the master endoscope 40, the master endoscope 40 and the slave endoscope 401 are in the same viewing direction. With respect to the viewing angle, that is, the imaging range, the imaging range of the master endoscope 40 is wider than the imaging range of the slave endoscope 401. In this case, the internal body site included in the slave endoscope image corresponds to (coincides with) the internal body site positioned in the central portion region of the master endoscope image. Consequently, by correcting the color tone in the master endoscope image and the slave endoscope image that have been acquired (imaged) at the point in time when the distal tip of the slave endoscope 401 is positioned at the distal tip portion 443 of the master endoscope 40 (at the point in time when the detection result is output) so as to reduce the difference between the color tone of a central part of the master endoscope image and the color tone of the slave endoscope image, the color tones (tints) of the master endoscope image and the slave endoscope image can be efficiently matched (approximated).

Second Embodiment

Figure 6:
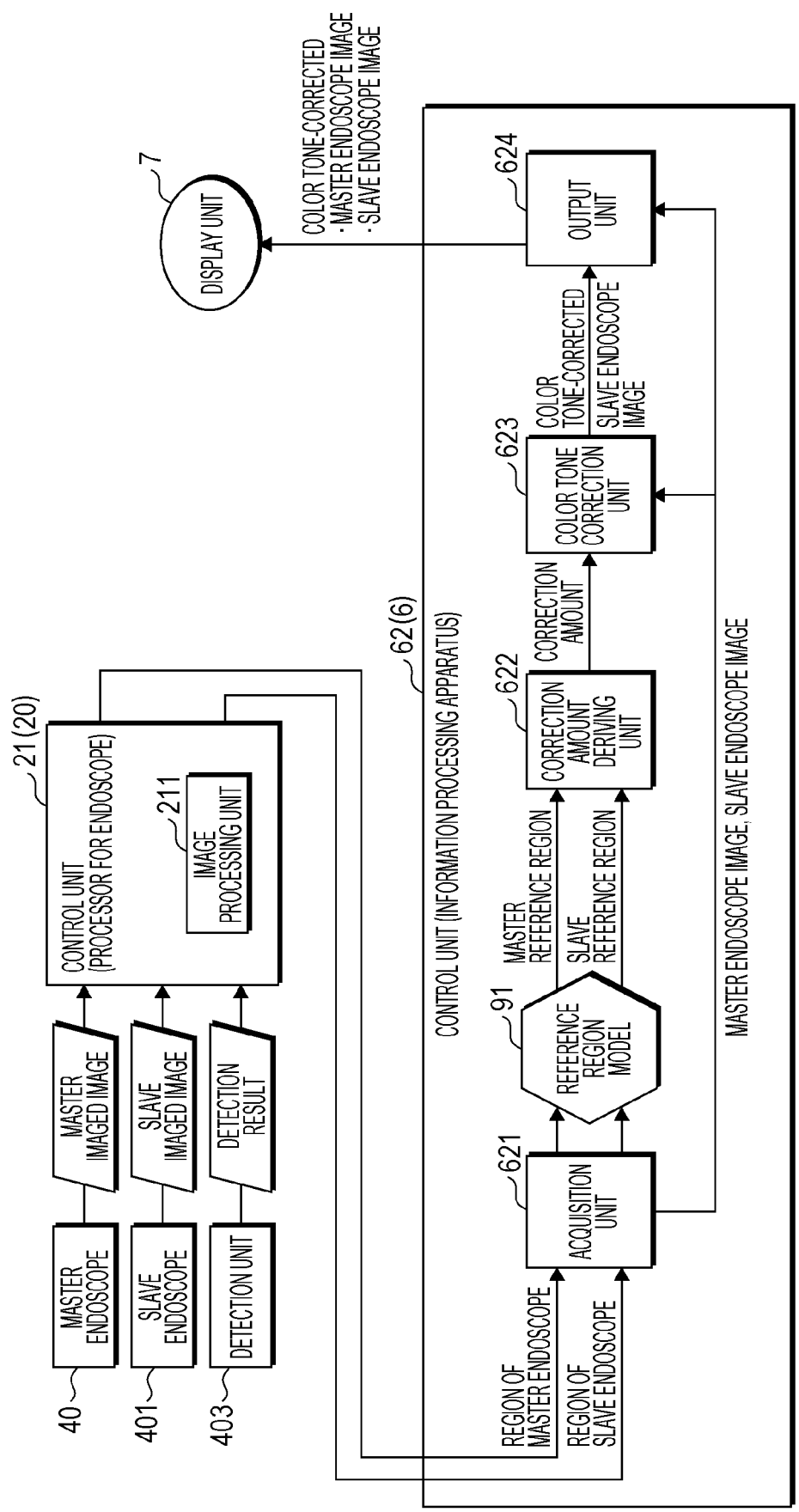
FIG. 6 is a functional block diagram that exemplifies functional units included in a control unit of the information processing apparatus according to a second embodiment (reference region model).

FIG. 6 is a functional block diagram that exemplifies functional units included in the control unit 62 of the information processing apparatus 6 according to the second embodiment (reference region model 91). By executing the program P (program product) stored in the storage unit 63, the control unit 62 of the information processing apparatus 6 functions as an acquisition unit 621, a correction amount deriving unit 622, a color tone correction unit 623, and an output unit 624. In addition, by executing the program P stored in the storage unit 63 or reading an entity file constituting the reference region model 91, the control unit 62 functions as the reference region model 91 (first learning model).

The acquisition unit 621 acquires the master endoscope image and the slave endoscope image output by the processor 20 for an endoscope, and the detection result output by a detection unit. The acquisition unit 621 inputs the master endoscope image and the slave endoscope image that have been acquired to the reference region model 91.

Figure 7:
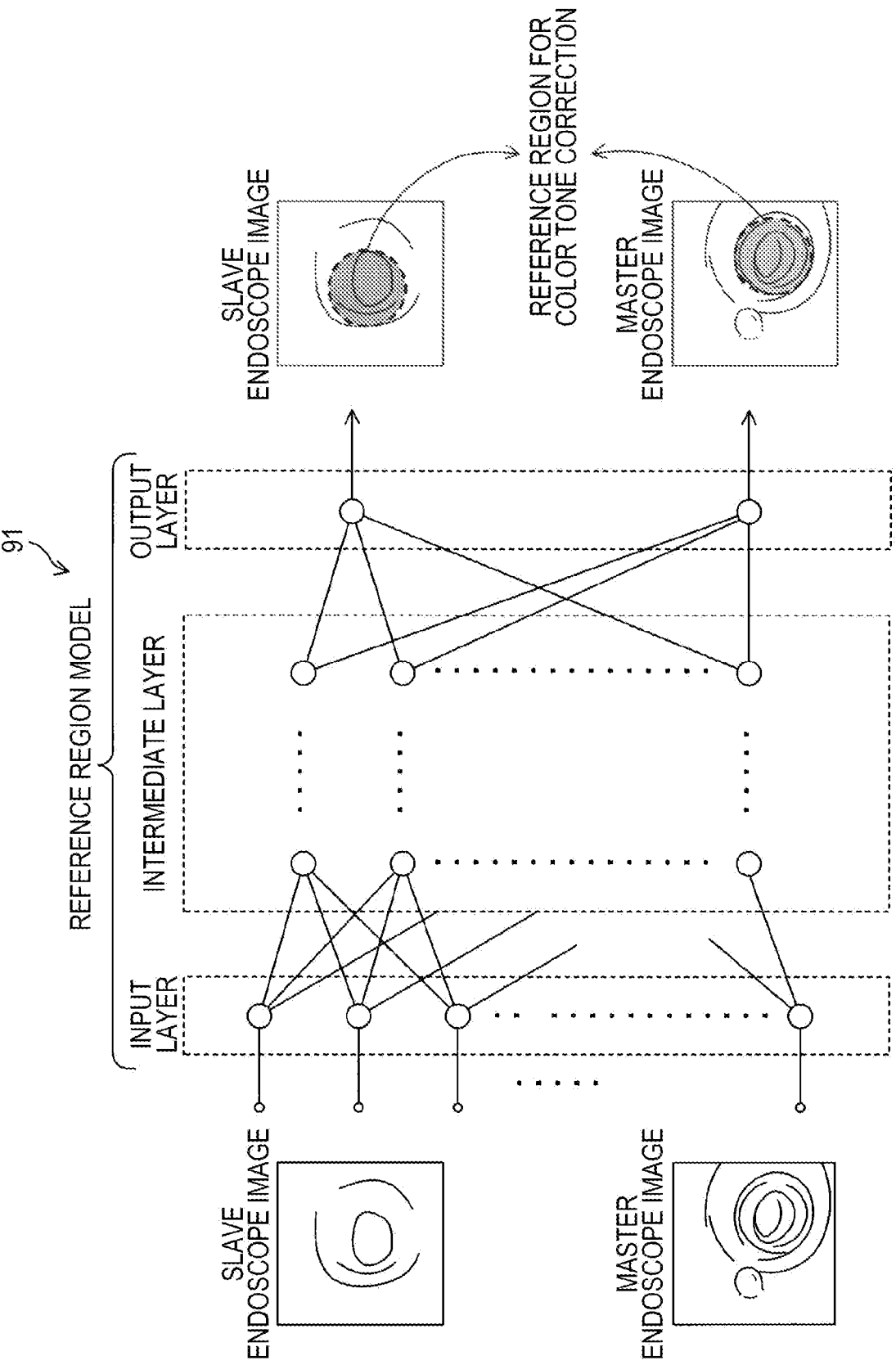
FIG. 7 is an explanatory diagram that explains a process of outputting respective regions serving as references for color tone correction using the reference region model.

FIG. 7 is an explanatory diagram that explains a process of outputting respective regions serving as references for color tone correction using the reference region model 91. The information processing apparatus 6 configures (generates) a neural network (reference region model 91), which is set to input the master endoscope image and the slave endoscope image and output information on the regions serving as references for color tone correction by learning based on training data in which the master endoscope image and the slave endoscope image are set as inquiry data and the regions serving as references for color tone correction in both these images are set as answer data. The master endoscope image and the slave endoscope image included in the answer data and indicating the regions serving as references for color tone correction can be acquired (prepared) by, for example, marking (annotating) regions having the same color tone based on the findings of a doctor or the like in the master endoscope images and the slave endoscope images stored in a large amount at a medical institution. It is assumed that the reference region model 91 learned using the training data is used as a program module, which is one part of an artificial intelligence software.

The reference region model 91 is configured by, for example, a neural network (segmentation NN) such as YOLO or R-CNN that performs region detection, semantic segmentation, or instance segmentation. An input layer has a plurality of neurons that receives input of the pixel values of the master endoscope image and the slave endoscope image, and transfers the input pixel values to an intermediate layer. The intermediate layer has a plurality of neurons that extracts image feature amounts of the master endoscope image and the slave endoscope image, and transfers the extracted image feature amounts of both individual images to an output layer. The output layer has one or a plurality of neurons that output each respective region in which the difference in color tone is equal to or less than a predetermined value in the extracted image feature amounts of both individual images, and outputs information related to the regions in which the difference in color tone is equal to or less than the predetermined value based on the image feature amounts of both individual images output from the intermediate layer. The reference region model 91 has been set as a segmentation NN, however it is not limited hereto, and may be a trained model having a configuration such as a fully convolution network (FCN) like U-Net, SegNet, SSD, SPPnet, a support vector machine (SVM), a Bayesian network, or a regression tree.

When the master endoscope image and the slave endoscope image are input, the reference region model 91 is trained to output respective regions serving as references for the color tone correction of the respective internal body sites included in the master endoscope image and the slave endoscope image. The respective regions serving as references for the color tone correction output by the reference region model 91 are the regions of the internal body site in the master endoscope image and the slave endoscope image in which these actual color tones in the internal body sites are estimated to be the same (tints are the same). Note that "the same actual color tone (tints are the same)" is not limited to a case of being completely the same, and may include cases where a difference amount is at an extent that is permitted when color tone correction is performed on the master endoscope image and the slave endoscope image. When regions (reference regions) of the internal body sites having the same actual color tone are present (included) in the master endoscope image and the slave endoscope image that have been input, the reference region model 91 outputs label images indicating the regions in each of the master endoscope image and the slave endoscope image. In the present embodiment, a single reference region model 91 has been set to output the label images indicating the reference regions in each of the master endoscope image and the slave endoscope image, however the present invention is not limited hereto. When the master endoscope image and the slave endoscope image are input, the reference region model 91 may include two reference region models 91, that is, a reference region model 91 for the master endoscope image that outputs the label images indicating the reference regions in the master endoscope image, and a reference region model 91 for the slave endoscope image that outputs the label images indicating the reference regions in the slave endoscope image.

The correction amount deriving unit 622 acquires the master endoscope image and the slave endoscope image in which the reference regions have been labeled from the reference region model 91. The correction amount deriving unit 622 specifies each pixel included in the labeled reference regions in the master endoscope image and the slave endoscope image, derives the difference values of the RGB components (intensities) between a pixel of the master endoscope image and a pixel of the slave endoscope image that have been specified, then derives the correction amounts based on the difference values in the same way as the first embodiment.

The color tone correction unit 623 corrects the color tone of the slave endoscope image by using the correction amount derived by the correction amount deriving unit 622 to convert the pixel value (RGB intensity) of each pixel of the slave endoscope image in the same way as the first embodiment. Deriving the correction amounts and color tone correction using the correction amounts, which are respectively performed by the correction amount deriving unit 622 and the color tone correction unit 623, are not limited to application only to the slave endoscope image (one-way correction to the master side) in the same way as the first embodiment, but may be applied to the master endoscope image (one-way correction to the slave side) or applied to the master endoscope image and the endoscope image (two-way correction).

In the same way as the first embodiment, the output unit 624 outputs the master endoscope image and the slave endoscope image subjected to processing related to this color tone correction to, for example, the display unit 7.

Figure 8:
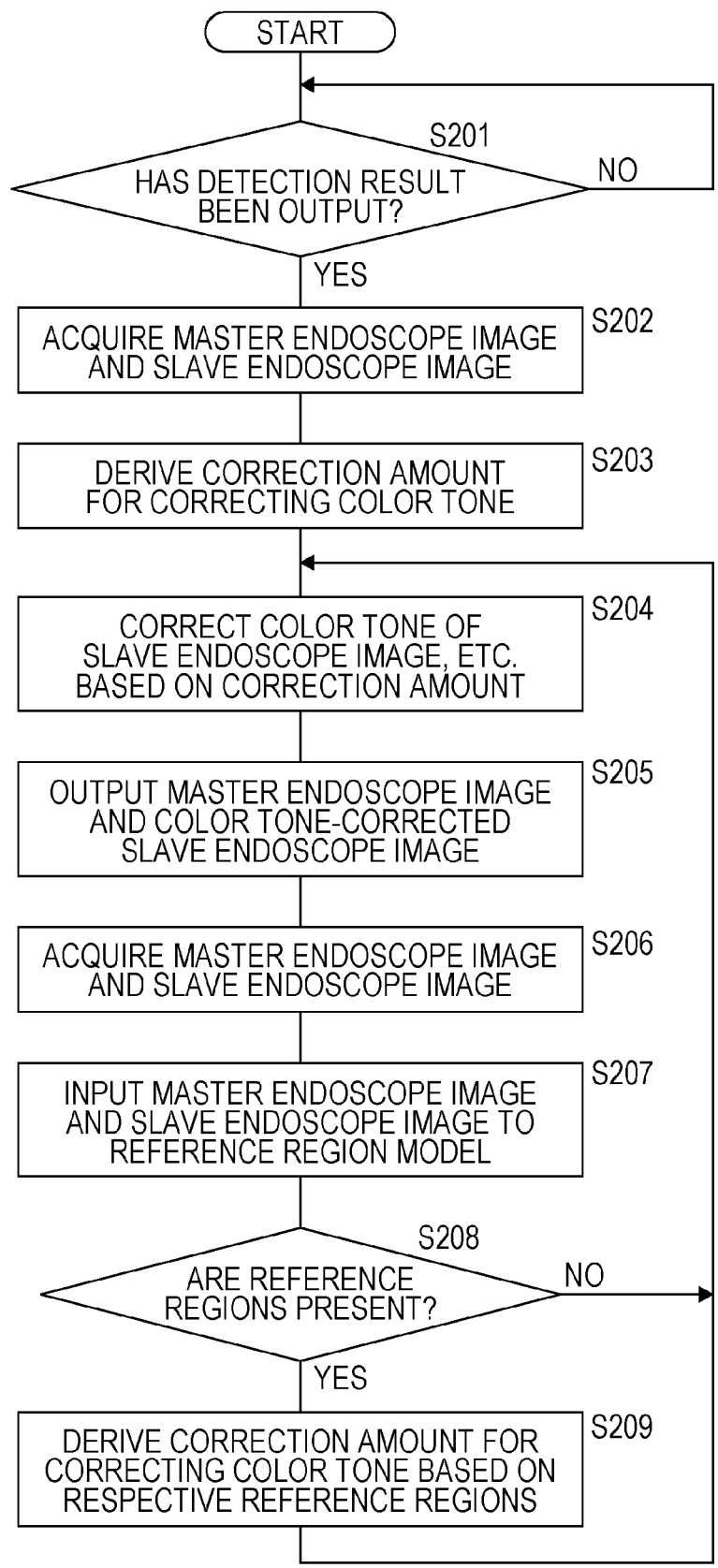
FIG. 8 is a flowchart that illustrates one example of a processing procedure executed by the control unit of the information processing apparatus.

FIG. 8 is a flowchart that illustrates one example of a processing procedure performed by the control unit 62 of the information processing apparatus 6. The control unit 62 of the information processing apparatus 6 starts processing of the flowchart based on, for example, contents input from the input unit 8 connected to the local device.

The control unit 21 of the processor 20 for an endoscope determines whether or not a detection result has been output from the detection unit 403 (S201). The control unit 21 of the processor 20 for an endoscope acquires the master endoscope image and the slave endoscope image (S202). The control unit 21 of the processor 20 for an endoscope derives the correction amounts for correcting the color tone based on the central portion of the master endoscope image and the slave endoscope image that have been acquired (S203). The control unit 21 of the processor 20 for an endoscope corrects the color tone of the slave endoscope image or the like based on the derived correction amounts (S204). The control unit 21 of the processor 20 for an endoscope outputs the master endoscope image and the color tone-corrected slave endoscope image (S205). The control unit 21 of the processor 20 for an endoscope acquires the master endoscope image and the slave endoscope image (S206). The control unit 21 of the processor 20 for an endoscope performs the processes from S201 to S206 in the same way as S101 to S106 of the first embodiment.

The control unit 21 of the processor 20 for an endoscope inputs the master endoscope image and the slave endoscope image that have been acquired to the reference region model 91 (S207). When regions (reference regions) of the internal body sites having the same actual color tone are present (included) in the master endoscope image and the slave endoscope image that have been input, the reference region model 91, for example, outputs label images indicating the reference regions or information related to the pixels included in the reference regions to each of the master endoscope image and the slave endoscope image. When regions (reference regions) of the internal body sites having the same actual color tone are not present (not included) in the master endoscope image and the slave endoscope image that have been input, the reference region model 91 does not output information related to the reference regions.

The control unit 21 of the processor 20 for an endoscope determines whether or not reference regions are present in the master endoscope image and the slave endoscope image that have been acquired (S208). The control unit 21 of the processor 20 for an endoscope determines whether or not reference regions are present based on a result output from the reference region model 91. When the information related to the reference regions is acquired from the reference region model 91, the control unit 21 of the processor 20 for an endoscope determines that reference regions are present. When the information related to the reference regions is not acquired from the reference region model 91, the control unit 21 of the processor 20 for an endoscope determines that reference regions are not present. When reference regions are not present (S208: NO), the control unit 21 of the processor 20 for an endoscope performs loop processing to execute the processes from S204 again. In this case, the color tone correction on the slave endoscope image or the like is performed using the correction amounts stored in the storage unit 63 at the current time.

When reference regions are present (S208: YES), the control unit 21 of the processor 20 for an endoscope derives the correction amounts for correcting the color tone based on the respective reference regions included in each of the master endoscope image and the slave endoscope image (S209). The control unit 21 of the processor 20 for an endoscope derives the correction amounts based on the reference regions by comparing the pixels included in the respective reference regions of the master endoscope image and the slave endoscope image in the same way as the first embodiment. By storing the derived correction amounts in the storage unit 63, the control unit 21 of the processor 20 for an endoscope updates the correction amounts used for the previous color tone correction with the correction amounts derived this time. After executing the processing of S209, the control unit 21 of the processor 20 for an endoscope performs loop processing to execute the processing from S204 again. By doing so, subsequent color tone correction is performed using the correction amounts derived (updated) this time.

In the present embodiment, etc., a series of processes have been described by dividing the processes into those implemented by the control unit 21 of the processor 20 for an endoscope and those implemented by the control unit 62 of the information processing apparatus 6, however the division of this processing is one example, and the present invention is not limited hereto. In the same way as the first embodiment, the control unit 21 of the processor 20 for an endoscope may function as all the functional units implemented by the control unit 62 of the information processing apparatus 6, including the reference region model 91. Alternatively, the control unit 21 of the processor 20 for an endoscope and the control unit 62 of the information processing apparatus 6 may function in cooperation as each functional unit in the series of processes by performing, for example, inter-process communication.

According to the present embodiment, etc., even when the field of view of the master endoscope image (the internal body site included in the master endoscope image) and the field of view of the slave endoscope image (the internal body site included in the slave endoscope image) are different from each other, it is also possible to correct the color tones of the master endoscope image and the slave endoscope image in accordance with the respective regions serving as references of the color tone correction output by the reference region model 91.

Third Embodiment

Figure 9:
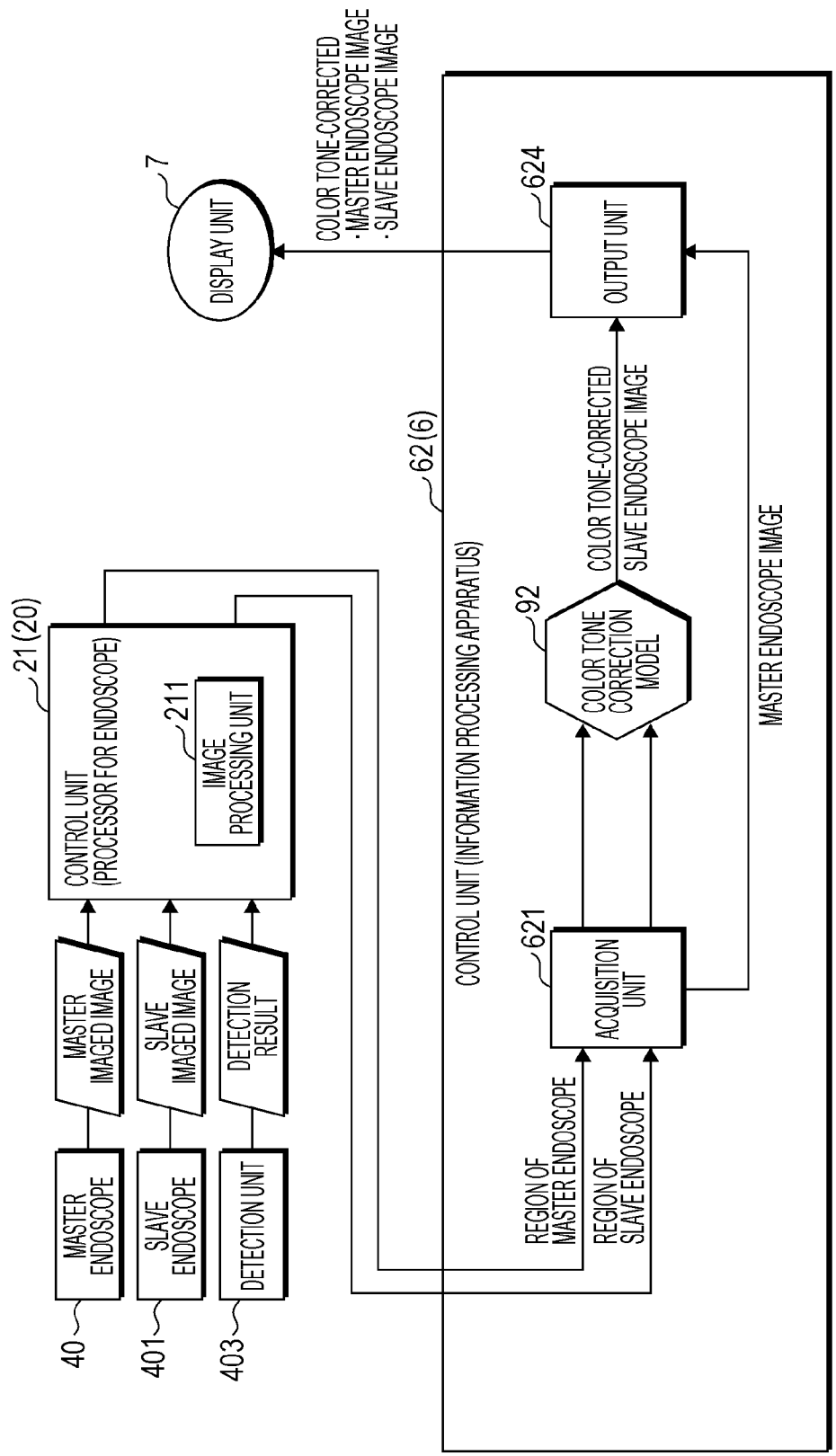
FIG. 9 is a functional block diagram that exemplifies functional units included in a control unit of the information processing apparatus according to a third embodiment (color tone correction model).

FIG. 9 is a functional block diagram that exemplifies the functional units included in the control unit 62 of the information processing apparatus 6 according to a third embodiment (color tone correction model 92). The control unit 62 of the information processing apparatus 6 functions as the acquisition unit 621 and the output unit 624 by executing the program P (program product) stored in the storage unit 63. In addition, the control unit 62 functions as the color tone correction model 92 by executing the program P stored in the storage unit 63 or by reading an entity file constituting the color tone correction model 92 (second learning model).

In the same way as the second embodiment, the acquisition unit 621 acquires the master endoscope image and the slave endoscope image output by the processor 20 for an endoscope, and the detection result output by the detection unit. The acquisition unit 621 inputs the master endoscope image and the slave endoscope image that have been acquired to the color tone correction model 92.

Figure 10:
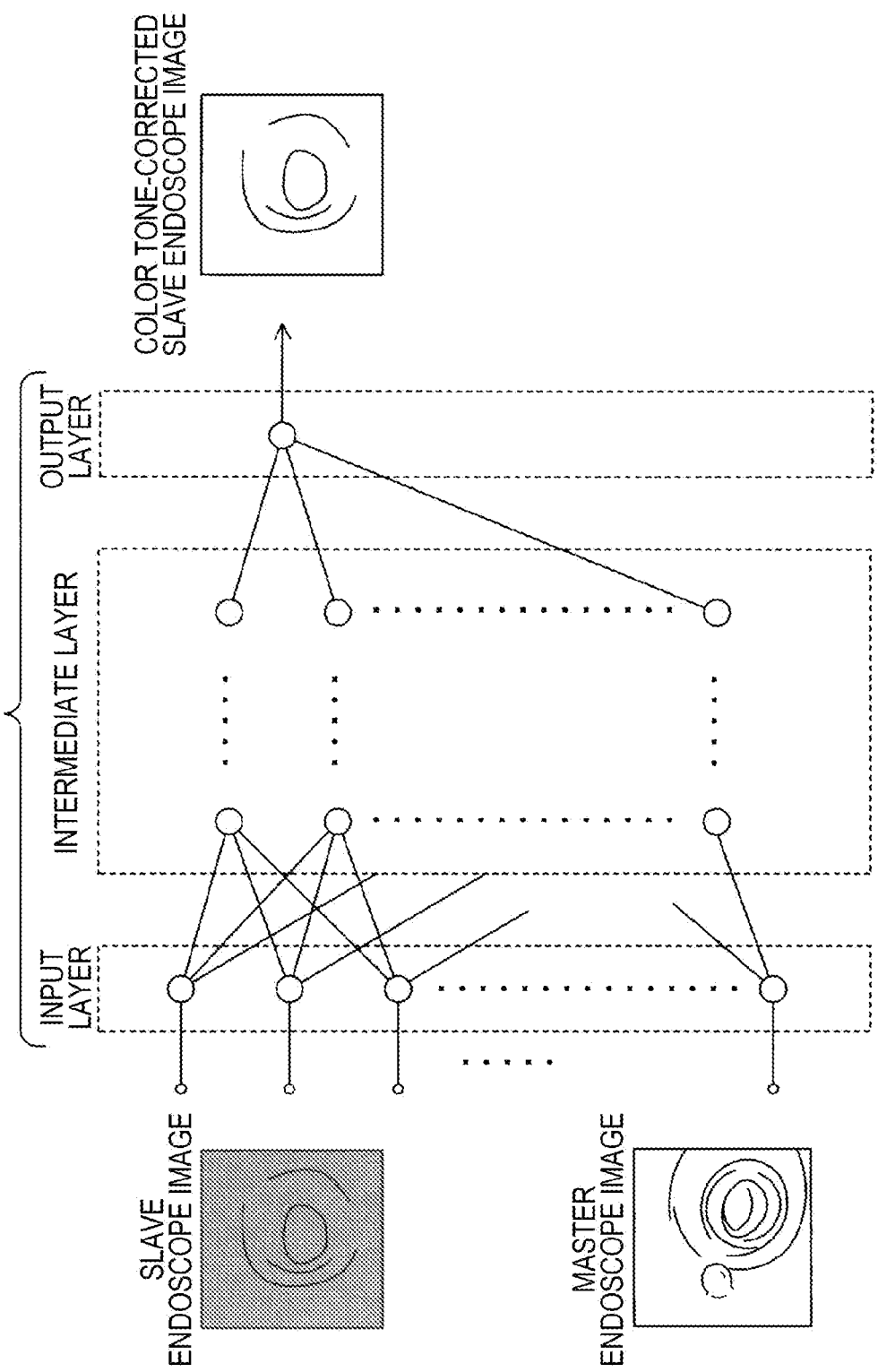
FIG. 10 is an explanatory diagram that explains a process of outputting the master endoscope image and the slave endoscope image for which the color tone has been corrected using the color tone correction model.

FIG. 10 is an explanatory diagram that explains a process of outputting the master endoscope image and the slave endoscope image for which the color tone has been corrected using the color tone correction model 92. The information processing apparatus 6 configures (generates) a neural network (color tone correction model 92), which is set to input the master endoscope image and the slave endoscope image and output the slave endoscope image in which a difference in color tone from the master endoscope image is reduced, by learning based on training data in which the master endoscope image and the slave endoscope image are set as inquiry data and the color tone-corrected slave endoscope image is set as answer data. The color tone-corrected slave endoscope image included in the answer data can be obtained (prepared) by using, for example, a slave endoscope image whose color tone has been corrected by the first embodiment. It is assumed that the color tone correction model 92 learned using the training data is used as a program module, which is one part of an artificial intelligence software.

The color tone correction model 92 is configured by, for example, a CNN autoencoder having a style conversion function. When the master endoscope image and the slave endoscope image are input and the color tone of the slave endoscope image is corrected, the master endoscope image corresponds to a reference image, while the slave endoscope image corresponds to a target image. The color tone correction model 92 is provided with an input layer, an intermediate layer, and an output layer in the same way as the reference region model 91 of the first embodiment. An input layer has a plurality of neurons that receives input of the pixel values of the master endoscope image and the slave endoscope image, and transfers the input pixel values to an intermediate layer. The intermediate layer extracts and dimensionally compresses (encodes) the image feature amounts of the slave endoscope image, which is the target image, and transfers the image feature amounts to the output layer together with the image feature amounts of the master endoscope image, which is the reference image. By factoring in the image feature amounts of the master endoscope image and decoding the feature amounts of the slave endoscope image subjected to dimension compression (encoding), the output layer outputs the slave endoscope image in which the difference in color tone from the master endoscope image is reduced. The color tone correction model 92 has been set as a CNN autoencoder, however it is not limited hereto, and may be a trained model having a configuration such as a GAN, an LSTM, or an RNN.

When the master endoscope image and the slave endoscope image are input, the color tone correction model 92 is trained to output the slave endoscope image in which the difference in color tone from the master endoscope image is reduced. Consequently, by using the color tone correction model 92, it is possible to acquire the slave endoscope image for which the color tone has been corrected so as to reduce the difference in color tone from the master endoscope image. In the present embodiment, the color tone correction model 92 has been set to output the slave endoscope image in which the difference in color tone from the master endoscope image is reduced, however it is not limited hereto, and may output the master endoscope image in which the difference in color tone from the slave endoscope image is reduced. Alternatively, when the master endoscope image and the slave endoscope image are input, the color tone correction model 92 may output the master endoscope image and the slave endoscope image in which the difference in color tone between both images is reduced.

The output unit 624 outputs the master endoscope image and the slave endoscope image on which the processing related to the color tone correction has been performed using the color tone correction model 92 to, for example, the display unit 7 in the same way as the first or second embodiment, etc.

Figure 11:
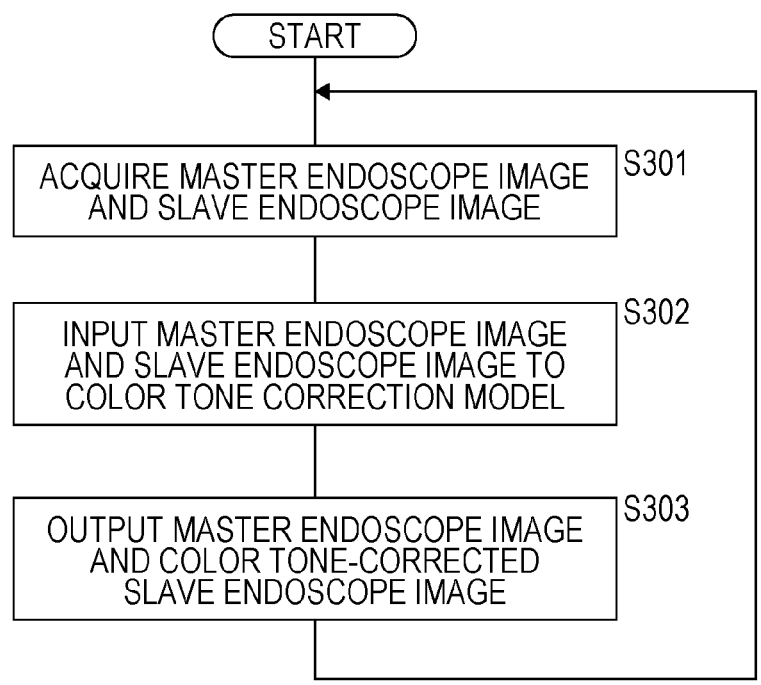
FIG. 11 is a flowchart that illustrates one example of a processing procedure executed by the control unit of the information processing apparatus.

FIG. 11 is a flowchart that illustrates one example of a processing procedure performed by the control unit 62 of the information processing apparatus 6. The control unit 62 of the information processing apparatus 6 starts processing of the flowchart based on, for example, contents input from the input unit 8 connected to the local device.

The control unit 21 of the processor 20 for an endoscope acquires the master endoscope image and the slave endoscope image (S301). The control unit 21 of the processor 20 for an endoscope performs the processing of S301 in the same way as S202 of the second embodiment.

The control unit 21 of the processor 20 for an endoscope inputs the master endoscope image and the slave endoscope image that have been acquired to the color tone correction model 92 (S302). When the master endoscope image and the slave endoscope image are input, the color tone correction model 92 outputs the slave endoscope image in which the difference in color tone from the master endoscope image is reduced. By using the color tone correction model 92, the control unit 21 of the processor 20 for an endoscope can acquire the slave endoscope image for which the color tone has been corrected so as to reduce the difference in color tone from the master endoscope image.

The control unit 21 of the processor 20 for an endoscope outputs the master endoscope image and the color tone-corrected slave endoscope image (S303). The control unit 21 of the processor 20 for an endoscope outputs the master endoscope image, and the slave endoscope image for which the color tone has been corrected so as to reduce the difference in color tone from the master endoscope image, to the display unit 7. As described above, when the color tone correction model 92 is trained to output the master endoscope image for which the color tone has been corrected so as to reduce the difference in color tone from the slave endoscope image, the control unit 21 of the processor 20 for an endoscope may output the color tone-corrected master endoscope image, or the color tone-corrected master endoscope image and the slave endoscope image to the display unit 7. In this way, the control unit 21 of the processor 20 for an endoscope outputs the master endoscope image and the slave endoscope image on which the processing related to the color tone correction model 92 has been performed and the difference in color tone is reduced to the display unit 7.

In the present embodiment, etc., a series of processes have been described by dividing the processes into those implemented by the control unit 21 of the processor 20 for an endoscope and those implemented by the control unit 62 of the information processing apparatus 6, however the division of this processing is one example, and the present invention is not limited hereto. In the same way as the first embodiment, the control unit 21 of the processor 20 for an endoscope may function as all the functional units implemented by the control unit 62 of the information processing apparatus 6, including the color tone correction model 92. Alternatively, the control unit 21 of the processor 20 for an endoscope and the control unit 62 of the information processing apparatus 6 may function in cooperation as each functional unit in the series of processes by performing, for example, inter-process communication.

According to the present embodiment, etc., by using the color tone correction model 92, it is possible to acquire the master endoscope image and the slave endoscope image having a smaller difference in color tone than the difference in color tone between the master endoscope image and the slave endoscope image input to the color tone correction model 92. By doing so, it is possible to efficiently perform the color tone correction on the master endoscope image and the slave endoscope image.

Fourth Embodiment

Figure 12:
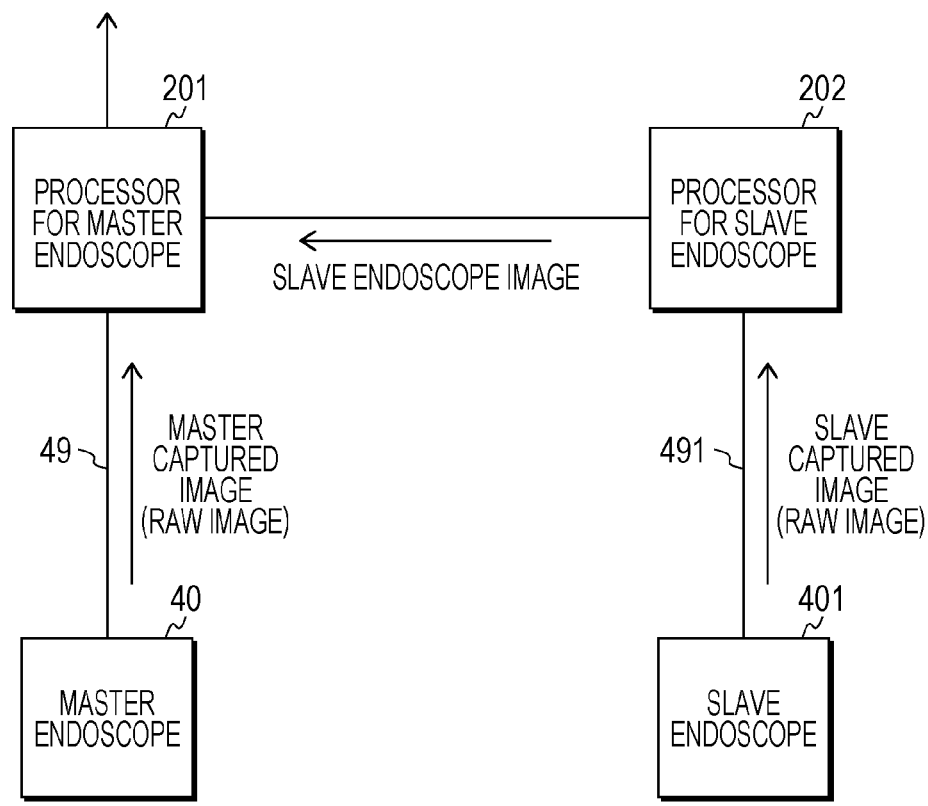
FIG. 12 is a block diagram that illustrates a configuration example of the endoscope system according to a fourth embodiment (processor for a master endoscope, processor for a slave endoscope).

FIG. 12 is a block diagram that illustrates a configuration example of the endoscope system according to a fourth embodiment (processor 201 for a master endoscope, processor 202 for a slave endoscope). The processor 20 for an endoscope of the fourth embodiment includes the processor 201 for a master endoscope connected to the master endoscope 40 and the processor 202 for a slave endoscope connected to the slave endoscope 401.

The processor 201 for a master endoscope and the processor 202 for a slave endoscope are provided with hardware functional units for converting captured images (master captured image and slave captured image) to endoscope images (master endoscope image, slave endoscope image), such as the control unit 21 (master control unit, slave control unit) and the main storage device 22, in the same way as the first embodiment.

The processor 202 for a slave endoscope converts the slave captured image transmitted from the slave endoscope 401 via the slave endoscope universal cord 491 to a slave endoscope image and outputs the slave endoscope image to the processor 201 for a master endoscope.

The processor 201 for a master endoscope converts the master captured image transmitted from the master endoscope 40 via the master endoscope universal cord 49 to a master endoscope image. Further, the processor 201 for a master endoscope performs the color tone correction on the slave endoscope image output from the processor 202 for a slave endoscope in the same way as the first embodiment, etc. to reduce the difference in color tone between the master endoscope image and the slave endoscope image. The processor 201 for a master endoscope outputs the master endoscope image and the slave endoscope image in which the difference in color tone is reduced by the color tone correction to, for example, the display device.

According to the present embodiment, since the processes related to the color tone correction are performed by the processor 201 for a master endoscope, it is possible to achieve equilibrium in load balance between the processor 201 for a master endoscope and the processor 202 for a slave endoscope by biasing the arithmetic processing amount to the processor 201 for a master endoscope having a comparatively high processing capability relative to the processor 202 for a slave endoscope.

It should be noted that the embodiments disclosed herein are illustrative in all respects and are not restrictive. The technical features described in the embodiments can be combined with each other, and the scope of the present invention is intended to include all modifications within the scope of the claims and the scope equivalent to the claims.

REFERENCE SIGNS LIST

S Endoscope system
10 Endoscope apparatus
15 Keyboard
16 Storage shelf
20 Processor for an endoscope
201 Processor for a master endoscope
202 Processor for a slave endoscope
21 Control unit
211 Image processing unit
22 Main storage device
23 Auxiliary storage device
24 Communication unit
25 Touch panel
26 Display device I/F
27 Input device I/F
28 Reading unit
31 Endoscope connector
311 Electrical connector
312 Optical connector
33 Light source
34 Pump
35 Water supply tank
36 Air/water supply port
40 Master endoscope
400 Master endoscope measurement unit
401 Slave endoscope
402 Slave endoscope measurement unit
403 Detection unit
43 Operation unit
431 Control button
433 Bending knob
434 Automatic operation mechanism
435 Forceps port
44 Insertion portion (flexible tube)
441 Soft portion
442 Bending section
443 Distal tip portion
444 Imaging unit
445 Image sensor
446 Imaging light source
45 Bend preventing portion
48 Scope connector
49 Master endoscope universal cord
491 Slave endoscope universal cord
50 Display device
6 Information processing apparatus
61 Communication unit
62 Control unit
621 Acquisition unit
622 Correction amount deriving unit
623 Color tone correction unit
624 Output unit
63 Storage unit
632 Recording medium
P Program
64 Input/output I/F
7 Display unit
8 Input unit
91 Reference region model (first learning model)
92 Color tone correction model (second learning model)

The invention claimed is:

1. A non-transitory computer-readable storage medium that stores an executable program for causing a computer communicatively connected to an endoscope apparatus including a master endoscope and a slave endoscope to execute processing comprising:

acquiring a master endoscope image of a subject from the master endoscope;

acquiring a slave endoscope image of the subject from the slave endoscope; and correcting a color tone of at least either one endoscope image of the master endoscope image and the slave endoscope image so as to reduce a difference in color tone between the master endoscope image and the slave endoscope image that have been acquired, wherein:

the slave endoscope is configured to protrude from a distal tip portion of the master endoscope, and a color tone of at least either one endoscope image of the master endoscope image and the slave endoscope image is corrected based on the master endoscope image and the slave endoscope image that are acquired when a detection result indicating that the slave endoscope protrudes from the distal tip portion of the master endoscope is output from a detector provided at the distal tip portion of the master endoscope.

2. The storage medium according to claim 1, wherein a color tone of at least either one endoscope image of the master endoscope image and the slave endoscope image is corrected so as to reduce a difference between a color tone of a central part of the master endoscope image and a color tone of the slave endoscope image.

3. The storage medium according to claim 1, wherein when a master endoscope image and a slave endoscope image are input, the master endoscope image and the slave endoscope image that have been acquired are input to a first learning model trained to output respective regions serving as references for color tone correction of respective internal body sites included in the master endoscope image and the slave endoscope image, a region of an internal body site included in the master endoscope image and a region of an internal body site included in the slave endoscope image are acquired from the first learning model, and a color tone of at least either one endoscope image of the master endoscope image and the slave endoscope image is corrected so as to reduce a difference between a color tone of the region of the internal body site included in the master endoscope image and a color tone of the region of the internal body site included in the slave endoscope image.

4. The storage medium according to claim 1, wherein correction amounts are derived based on difference values between corresponding pixels of the master endoscope image and the slave endoscope image that have been acquired, and a color tone of at least either one endoscope image of the master endoscope image and the slave endoscope image is corrected using the correction amounts that have been derived.

5. The storage medium according to claim 1, wherein when a master endoscope image and a slave endoscope image are input, color tone correction is performed by inputting the master endoscope image and the slave endoscope image that have been acquired to a second learning model trained to output a master endoscope image or a slave endoscope image having a smaller difference in color tone than a difference in color tone between the master endoscope image and the slave endoscope image that have been input.

6. The storage medium according claim 1, wherein the master endoscope image and the slave endoscope image in which the difference in color tone is reduced by the color tone correction are output.

7. An information processing method for causing a computer communicatively connected to an endoscope apparatus including a master endoscope and a slave endoscope to execute processing comprising:

acquiring a master endoscope image of a subject from the master endoscope;

acquiring a slave endoscope image of the subject from the slave endoscope; and correcting a color tone of at least either one endoscope image of the master endoscope image and the slave endoscope image so as to reduce a difference in color tone between the master endoscope image and the slave endoscope image that have been acquired, wherein:

the slave endoscope is configured to protrude from a distal tip portion of the master endoscope, and a color tone of at least either one endoscope image of the master endoscope image and the slave endoscope image is corrected based on the master endoscope image and the slave endoscope image that are acquired when a detection result indicating that the slave endoscope protrudes from the distal tip portion of the master endoscope is output from a detector provided at the distal tip portion of the master endoscope.

8. An endoscope system including an endoscope apparatus and controllers that process endoscope images of a subject that is imaged, the endoscope apparatus comprising:

a master endoscope;

a slave endoscope that protrudes from a distal tip portion of the master endoscope; and a detector provided at the distal tip portion of the master endoscope and which detects the slave endoscope, wherein a master endoscope image of the subject is acquired from the master endoscope, a slave endoscope image of the subject is acquired from the slave endoscope, a color tone of at least either one endoscope image of the master endoscope image and the slave endoscope image is corrected so as to reduce a difference in color tone between the master endoscope image and the slave endoscope image that have been acquired, and the controllers correct a color tone of at least either one endoscope image of the master endoscope image and the slave endoscope image based on the master endoscope image and the slave endoscope image acquired when the detection unit detects the slave endoscope.

9. The endoscope system according to claim 8, wherein the controllers include a slave controller that processes the slave endoscope image and a master controller that processes the master endoscope image, and the master controller acquires the slave endoscope image from the slave controller and corrects a color tone of at least either one endoscope image of the master endoscope image and the slave endoscope image so as to reduce a difference in color tone between the master endoscope image and the slave endoscope image that have been acquired.

* * * * *